United States Patent
Shibusawa et al.

(10) Patent No.: US 6,870,066 B2
(45) Date of Patent: Mar. 22, 2005

(54) METHOD FOR DECOMPOSITION OF MICHAEL TYPE ADDUCT

(75) Inventors: Fumio Shibusawa, Hyogo (JP); Naoki Serata, Himeji (JP); Kazuhiko Sakamoto, Kobe (JP)

(73) Assignee: Nippon Shokubai Co., LTD, Osaka (JP)

( * ) Notice: Subject to any disclaimer, the term of this patent is extended or adjusted under 35 U.S.C. 154(b) by 0 days.

(21) Appl. No.: 10/385,359

(22) Filed: Mar. 10, 2003

(65) Prior Publication Data

US 2003/0204106 A1 Oct. 30, 2003

(30) Foreign Application Priority Data

Apr. 25, 2002 (JP) ........................ 2002-124301

(51) Int. Cl.⁷ .................... C07C 69/73; C07C 57/18
(52) U.S. Cl. .................... 560/216; 560/205; 560/224; 560/260; 562/598; 562/599
(58) Field of Search ................ 560/216, 224, 560/260, 205; 562/598, 599

(56) References Cited

U.S. PATENT DOCUMENTS

| | | | |
|---|---|---|---|
| 2,393,737 A | 1/1946 | Bortnick | 560/212 |
| 2,806,878 A * | 9/1957 | Luber | 562/598 |
| 3,639,466 A | 2/1972 | Leichtle | |
| 3,868,410 A | 2/1975 | Horlenko et al. | |
| 3,954,854 A | 5/1976 | Gehrmann et al. | |
| 5,504,243 A * | 4/1996 | Sakamoto et al. | 560/205 |
| 6,498,272 B1 | 12/2002 | Schroder et al. | 562/600 |

FOREIGN PATENT DOCUMENTS

| | | |
|---|---|---|
| CN | 1046324 A | 10/1990 |
| EP | 0 685 447 A2 | 12/1995 |
| EP | 0 855 376 A1 | 7/1998 |
| EP | 0 887 334 A1 | 12/1998 |
| EP | 1 275 633 A2 | 1/2003 |
| GB | 2285983 * | 8/1995 |
| JP | A-57-62229 | 4/1982 |
| JP | A-03-178949 | 8/1991 |
| WO | WO 00/53560 | 9/2000 |

* cited by examiner

*Primary Examiner*—Cecilia J. Tsang
*Assistant Examiner*—Taylor V. Oh
(74) *Attorney, Agent, or Firm*—Mathews, Collins, Shepherd & McKay, P.A.

(57) ABSTRACT

A method for the decomposition of a Michael type adduct of an acrylic acid and/or an acrylic ester represented by the following formula [I] or [II] is disclosed, wherein decomposing the Michael type adduct in the presence of at least one copper salt and at least one metal salt selected from the group consisting of an alkali metal salt and an alkaline earth metal salt into an acrylic acid and/or an acrylic ester and/or an alcohol.

$$CH_2=CHCOO(-X-COO)_n-R^1 \qquad [I]$$

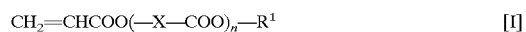

$$R^2-O(-X-COO)_m-R^3 \qquad [II]$$

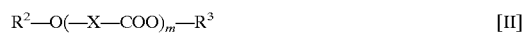

(wherein n and m denote an integer in the range of 1–5, $R^1$, $R^2$, and $R^3$ independently denote a hydrogen atom or an alkyl group, and —X— denotes —$CH_2CH_2$— or —CH($CH_3$)—, and —X— may be identical or different when n is 2 or more).

4 Claims, 2 Drawing Sheets

METHOD FOR DECOMPOSITION OF MICHAEL TYPE ADDUCT

BACKGROUND OF THE INVENTION

1. Field of the Invention

This invention relates to a method for the decomposition of a Michael type adduct of acrylic acid and/or an acrylic ester and more particularly to a method for the decomposition of a Michael type adduct by-produced by the action of heat or a catalyst during the production of acrylic acid and/or an acrylic ester, which method is characterized by decomposing the Michael type adduct into acrylic acid and/or an acrylic ester and/or an alcohol in the presence of a copper salt and an alkali metal salt or an alkaline earth metal salt.

2. Description of the Related Art

Generally, the production of acrylic acid and an ester thereof, while in process, possibly entails by-production of a Michael type adduct having a carboxylic acid or an alcohol added to the carbon-carbon double bond of acrylic acid or an acrylic ester owing to the action of heat or a catalyst. The Michael type adducts thus derived include polymers of a multiplicity in the approximate range of 2–5 of molecules of acrylic acid, esters thereof, alkoxypropionic acids, and alkoxypropionic esters, for example.

If the quantity of a Michael type adduct to be by-produced increases, this increase will result in lowering the efficiency of raw material and increasing the cost of production in the process for the production of acrylic acid. This situation is unfavorable. If the Michael adduct accumulates during the process, the accumulation will seriously hinder the step of purification and the step of production. Further, the occurrence of a by-product and the elevation of temperature will degrade the quality of the product. The practice of concentrating the Michael type adduct at the step of purification, discharging the concentrate out of the process system, and disposing of it by incineration is generally followed. This incineration, however, is unfavorable even from the viewpoint of the environmental preservation. In the process for the production of acrylic acid, efforts have been made to decompose the Michael type adduct and reclaim the product of this decomposition.

As a way of decomposing such a Michael type adduct, for example, a method which decomposes an oligomer of acrylic acid or an acrylic ester, an alkoxypropionic acid, or an alkoxypropionic ester by the action of heat or a catalyst has been known. Specifically, U.S. Pat. No. 3,868,410 discloses a method which decomposes a Michael type adduct by-produced during the esterification of acrylic acid with an alcohol into monomers by heating the adduct at a temperature of 180° C. or more. Then, U.S. Pat. No. 3,639,466 discloses a method which produces acrylic acid by heating the residue occurring in the finishing step of acrylic acid in the presence of a compound possessing a primary or tertiary amino group or in the presence of a tertiary phosphine as a catalyst.

These methods in operation, however, require fairly high temperatures and recover acrylic acid only with low percentages. When they are compelled to obtain acrylic acid with high recovery percentages, they encourage secondary reactions and yield large quantities of such by-products as high-boiling substances and low-boiling substances which degrade the quality of acrylic acid or an acrylic ester. After all, these methods do not easily recover acrylic acid with a high percentage.

Further, the JP-A-03-178949 discloses a method for recovering monomers from the Michael type adduct by-produced in the production of acrylic acid and an ester thereof by catalytically decomposing this adduct in the presence of a solid acid at an elevated temperature of 200° C. or more. By this method, the Michael type adduct is decomposed with a high percentage. This method, however, is unfavorable from the viewpoint of the quality of the product because the reaction proceeds at the elevated temperature and forms by-products such as low-boiling substances with high percentages. Since the decomposition proceeds in the form of a solid-liquid reaction, the catalytic activity is markedly degraded by poisoning. Furthermore, since the methods described above invariably concern reactions at elevated temperatures, they are fated to form highly viscous residues which will eventually solidify after a protracted retention. Thus, they are at a disadvantage in rendering the disposal of their residues very difficult.

Chinese Patent 1046324A discloses a method for recovering acrylic acid from a waste liquid containing acrylic acid and a dimer of acrylic acid by heating this waste liquid together with the process water, and following destructive distillation. This method aims to lower the viscosity of the waste liquid by the addition of the process water and facilitate the distillation of acrylic acid and the dimer of acrylic acid. The method of Chinese Patent 1046324A, however, has the problem that the thermal treatment of high temperature in the presence of water gives rise to polymers like polymer of acrylic acid, adds to the viscosity of there action solution, and aggravates adverse behaviors of the reaction solution as by gelation. Further, since the used process water must be isolated from the system, the manufacturing process will be complicated.

The JP-A-57-62229 discloses a method which consists in treating heavy substances by-produced during the production of an acrylic ester with an aqueous alkali solution. This method, however, forms a precipitate due to the treatment with the aqueous alkali solution and forms polymers such as polymer of acrylic acid due to the heat of neutralization. It, therefore, entails such problems as aggravating the condition of the reaction solution by thickening or gelation, and the problem caused disadvantage from the viewpoint of energy. Moreover, this method poses the problem of impairing the quality of the product owing to the by-products like β-hydroxy propionic acid.

In the circumstance, the development of a technique which is capable of converting the Michael type adduct into at least one compound selected from the group consisting of useful acrylic acid, esters thereof and alcohols, and recovering or reclaiming or reclaiming this useful compound efficiently has been being craved.

SUMMARY OF THE INVENTION

The present inventors have pursued a study in search of a method for decomposing the Michael type adduct which occurs in the process for the production of acrylic acid and esters thereof. They have consequently found that in the process of producing acrylic acid and so on, the presence of a copper salt and an alkali metal salt and/or an alkaline earth metal salt enables the Michael type adduct to be decomposed into useful components while precluding the problem of thickening and gelation of the reaction solution, and formation of by-products. This invention has been perfected as a result. It has not been known that the copper salt and the alkali metal salt or the alkaline metal salt possess the activity of decomposing the Michael type adduct in the production of acrylic acid and so on.

In accordance with this invention, the Michael type adduct reacts in the presence of a copper salt and an alkali metal salt and/or an alkaline earth metal salt and can be decomposed into acrylic acid. By incorporating this method of decomposition into the manufacturing process for acrylic acid, the efficiency of the raw material can be increased while preventing the thickening and gelation of the solution, the yield can be heighten.

DETAILED DESCRIPTION OF THE INVENTION

Figure 1:
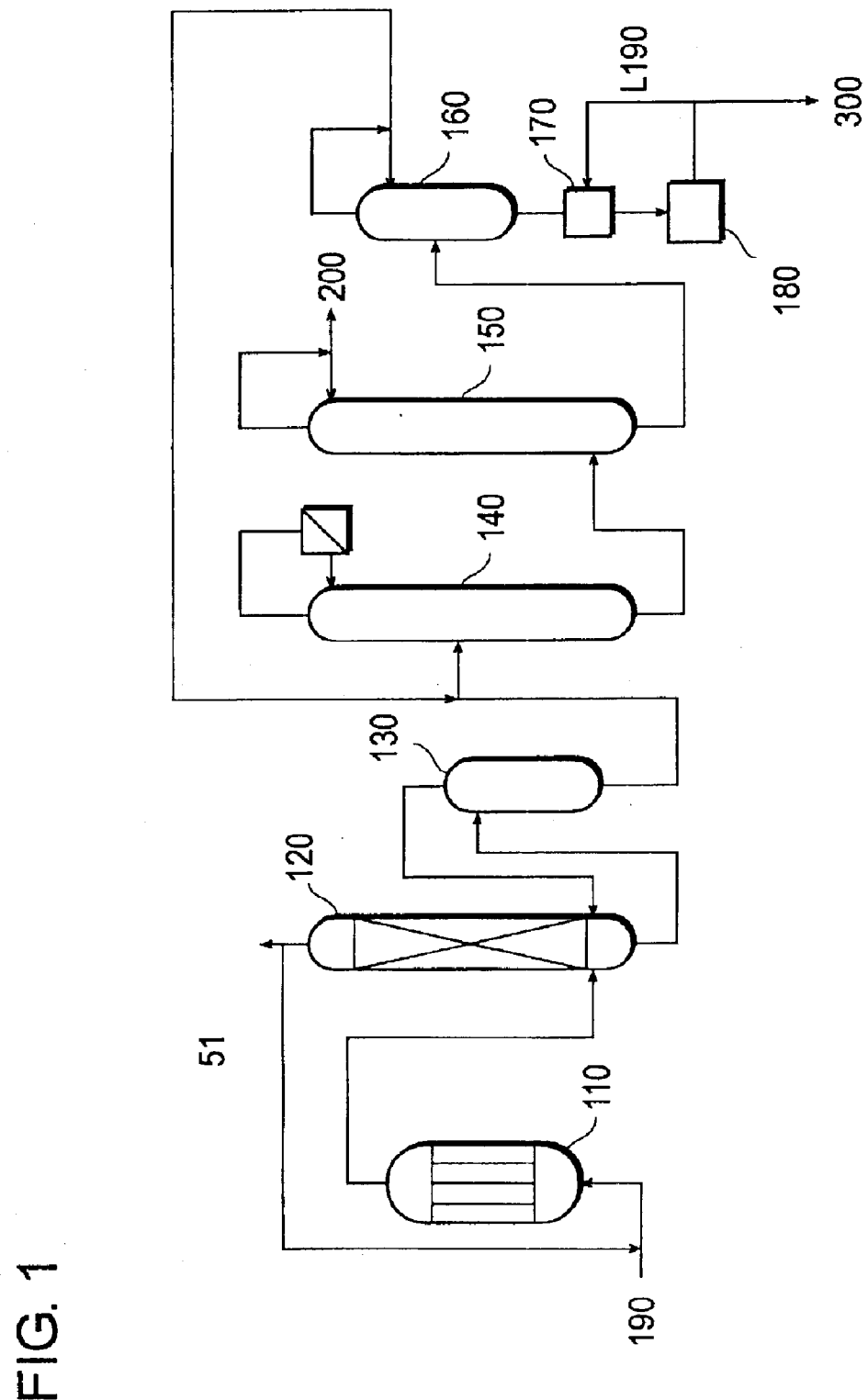
FIG. 1 is a schematic flow diagram showing the process for producing acrylic acid.

The first aspect of this invention concerns a method for the decomposition of a Michael type adduct of an acrylic acid and/or an acrylic ester represented by the following formula [I] or [II], wherein decomposing the Michael type adduct in the presence of at least one copper salt and at least one metal salt selected from the group consisting of an alkali metal salt and an alkaline earth metal salt into an acrylic acid and/or an acrylic ester and/or an alcohol.

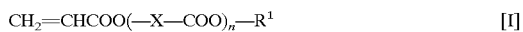

$$CH_2=CHCOO(-X-COO)_n-R^1 \quad [I]$$

(wherein n denotes an integer in the range of 1–5, $R^1$ denotes a hydrogen atom or an alkyl group, and —X— denotes —$CH_2CH_2$— or —$CH(CH_3)$—, and —X— may be identical or different when n is 2 or more).

$$R^2-O(-X-COO)_m-R^3 \quad [II]$$

(wherein m denotes an integer in the range of 1–5, $R^2$ and $R^3$ independently denote a hydrogen atom or an alkyl group, and —X— denotes —$CH_2CH_2$— or —$CH(CH_3)$—, and —X— maybe identical or different when n is 2 or more).

The alkyl groups denoted by $R^1$, $R^2$, and $R^3$ in the formulas [I] and [II] originate from the alcohols used as raw materials in the production of a relevant acrylic ester. Specifically, straight or branched alkyl groups, alkyl groups having an aromatic group substituted for the hydrogen atom of an alkyl group, and cyclic alkyl groups having a cycloalkyl group substituted for the hydrogen atom of an alkyl group may be cited as examples. As concrete examples of the alkyl groups which are denoted by $R^1$, $R^2$, and $R^3$, alkyl groups having 1–8 carbon atoms such as methyl, ethyl, n-butyl, t-butyl, propyl, 2-ethylhexyl, benzyl which has a phenyl group linked to methyl, and 2-cyclopentylmethyl group which has a cyclopentane linked to methyl may be cited. In this invention, $R^1$, $R^2$, and $R^3$ are preferred to denote independently a hydrogen atom, methyl, ethyl, n-butyl, t-butyl, or 2-ethylhexyl. This preference is because these compounds are those which are by-produced in the process for producing acrylic acid and an acrylic ester.

Then, "—X—" denotes —$CH_2CH_2$— or —$CH(CH_3)$— and n denotes an integer in the range of 1–5, preferably 1–2. This preference is because the process for producing acrylic acid and an acrylic ester by-produces their dimers and trimers with high percentages. The term "n" in Formula [I] denotes an integer in the range of 1–5, preferably 1–2. This preference is because the process for producing acrylic acid and an acrylic ester by-produces their dimers and trimers with high percentages. The term "m" in Formula [II] denotes an integer in the range of 1–5, preferably 1–2. This preference is because the process for producing an acrylic ester by-produces an alkoxypropionic acid and esters with high percentages. Such Michael type adducts are by-produced in the process for producing acrylic acid and acrylic esters. In accordance with this invention, they are efficiently recovered as a useful acrylic acid group compound, namely at least one compound selected from the group consisting of an acrylic acid, an acrylic ester, and an alcohol. By this invention, therefore, the substantial yield in the process for the production of acrylic acid and esters thereof can be increased.

In this invention, the Michael type adduct mentioned above is decomposed in the presence of a copper salt and an alkali metal salt and/or an alkaline earth metal salt. The copper salt is not particularly restricted but may be arbitrarily selected from a wide variety of compounds including both in organic salts and organic salts. As concrete examples of the copper salt, copper dialkyldithiocarbamate, copper acetate, copper naphthenate, copper acrylate, copper sulfate, copper nitrate, and copper chloride may be cited. The copper salts usable herein have a valence of either one or two. Among other copper salts, copper dialkyldithiocarbamates, copper alkylarylthiocarbamates, and copper diarylthiocarbamates prove particularly favorable from the viewpoint of effect.

As concrete examples of the copper dialkyldithiocarbamates, copper alkylarylthiocarbamates, and copper diarylthiocarbamates, copper dimethyldithiocarbamate, copper diethyldithiocarbamate, copper dipropyldithiocarbamate, copper dibutyldithiocarbamate, copper dipentyldithiocarbamate, copper dihexyldithiocarbamate, copper diphenyldithiocarbamate, copper methylethyldithiocarbamate, copper methylpropyldithiocarbamate, copper methylbutyldithiocarbamate, copper methylpentyldithiocarbamate, copper methylhexyldithiocarbamate, copper methylphenyldithiocarbamate, copper ethylpropyldithiocarbamate, copper ethylbutyldithiocarbamate, copper ethylpentyldithiocarbamate, copper ethylhexyldithiocarbamate, copper ethylphenyldithiocarbamate, copper propylbutyldithiocarbamate, copper propylpentyldithiocarbamate, copper propylhexyldithiocarbamate, copper propylphenyldithiocarbamate, copper butylpentyldithiocarbamate, copper butylhexyldithiocarbamate, copper butylphenyldithiocarbamate, copper pentylhexyldithiocarbamate, copper pentylphenyldithiocarbamate, and copper hexylphenyldithiocarbamate may be cited. These copper dialkyldithiocarbamates may be univalent copper salts or divalent copper salts. Among other copper dialkyldithiocarbamates enumerated above, copper dimethyldithiocarbamate, copper diethyldithiocarbamate, and copper dibutyldithiocarbamate prove favorable and copper dibutyldithiocarbamate proves particularly favorable from the viewpoints of effect and ease of procurement.

The alkali metal salt are salt of lithium, sodium, potassium, rubidium, cesium, and francium. The salt of lithium, sodium, and potassium are preferably used from the viewpoint of their excellent ability to decompose the Michael type adduct of acrylic acid. As concrete examples of the salt preferably used herein, acrylates such as sodium acrylate, potassium acrylate, and lithium acrylate; hydroxides such as sodium hydroxide, potassium hydroxide, and lithium hydroxide; hydrides such as sodium boron hydride and sodium hydride; halogenides such as sodium fluoride, sodium chloride, sodium bromide, and sodium iodide; oxygen compounds such as sodium peroxide and sodium hyperoxide; sulfides such as sodium sulfide; nitrogen compounds such as sodium amide and sodium azide; oxyacid salts such as sodium hypochlorite; alkoxides represented by RONa wherein R denotes an alkyl group of 1–5 carbon atoms, and sulfates, nitrates, phosphates, carbonates, silicates, oxalates, and acetates of alkali metals may be cited.

The alkaline earth metal salt are salt of beryllium, magnesium, calcium, strontium, barium, and radium. The salt of magnesium, calcium, and barium are preferably used from the viewpoint of their excellent ability to decompose the Michael type adducts of acrylic acid. As concrete examples of the alkaline earth metal salt used herein, acrylates such as calcium acrylate, magnesium acrylate, and barium acrylate; hydroxides such as calcium hydroxide, magnesium hydroxide, and barium hydroxide; hydrides such as calcium hydride; chlorides such as calcium fluoride and calcium chloride, and sulfates, nitrates, phosphates, carbonates, silicates, oxalates, and acetates of alkaline earth metals maybe cited. In this invention, acrylates of alkali metals or alkaline earth metals are preferably used. The reason for this preference is that the acrylic acid resulting from the dissociation of ions can be used as the target compound for production.

In this invention, the method for the addition of the copper salt and the alkali metal salt and/or the alkaline earth metal salt is not particularly restricted. One or more members selected from the groups consisting respectively of copper salt, and alkali metal salt and/or alkaline earth metal salt in a solid state may be added directly to the waste liquid containing the Michael type adduct of acrylic acid such as the dimer of acrylic acid, and acrylic acid. These selected compounds dissolved in a solvent may be added. The site of their introduction is not restricted. It is only required that the copper salt, and the alkali metal salt and/or the alkaline earth metal salt will be contained eventually in the waste liquid. The compounds mentioned above may be directly supplied to a decomposing tank for the Michael type adduct of acrylic acid. The copper salt, and the alkali metal salt and/or the alkaline earth metal salt, or the solutions thereof may be introduced into the decomposing tank via a pipe for circulation.

As a way of making these compounds function in the state of solution, for example, the practice of dissolving the copper salt, and the alkali metal salt and/or the alkaline earth metal salt in a proper solvent and supplying them in the form of a solution is followed. This solution may be delivered in a sprayed form. The solvents usable for the solution of the copper salt, and the alkali metal salt and/or the alkaline earth metal salt include acrylic acid, acrylic esters, alcohols such as methanol and ethanol, water, benzene, toluene, acetone, methylethyl ketone, and methylisobutyl ketone, and so on. These solvents may be used either singly or in the form of a mixture.

The quantity of the copper salt to be used in this case is in the range of 0.01–10 mass %, preferably 0.05–5 mass %, and particularly preferably 0.1–2 mass %, based on the mass of the waste liquid. If this quantity is less than 0.01 mass %, there is a possibility that the efficiency is degraded, and the efficiency of the conversion is not sufficient. Conversely, if the quantity exceeds 10 mass %, there is a possibility that a highly viscous residue is generated, and an industrially unfavorable situation is induced.

The total quantity of the alkali metal salt and/or the alkaline earth metal salt to be used herein is in the range of 0.01–10 mass %, preferably 0.05–5 mass %, and particularly preferably 0.1–2 mass %, based on the mass of the waste liquid. If this quantity is less than 0.01 mass %, there is a possibility that the efficiency is degraded, and the efficiency of the conversion is not sufficient. Conversely, if the quantity exceeds 10 mass %, there is a possibility that a highly viscous residue is generated, and an industrially unfavorable situation is induced.

In this invention, the use of an N-oxyl compound in addition to the at least one metal salt selected from the group consisting of alkali metal salt and alkaline metal salt plus the copper salt is permissible. Popularly known N-oxy compounds which possess a catalytic activity for decomposing the Michael type adduct are applicable for this additional use. Among the N-oxyl compounds, 4,4',4'-tris-(2,2,6,6-tetramethyl piperidinoxyl) phosphite and 2,2,6,6-tetramethyl piperidinoxyls represented by the following formula (1) are used particularly preferably either singly or in the form of mixture.

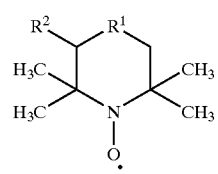

(1)

(wherein $R^1$ denotes $CH_2$, CHOH, $CHCH_2OH$, $CHCH_2CH_2OH$, $CHOCH_2OH$, $CHOCH_2CH_2OH$, CHCOOH, or C=O and $R^2$ denotes a hydrogen atom or $CH_2OH$).

In this invention, at least one of N-hydroxy-2,2,6,6-tetramethyl piperidine compounds such as 1,4-dihydroxy-2,2,6,6-tetramethyl piperidine and 1-hydroxy-2,2,6,6-tetramethyl piperidine, or at least one of 2,2,6,6-tetramethyl piperidine compounds such as 2,2,6,6-tetramethyl piperidine and 4-hydroxy-2,2,6,6-tetramethyl piperidine can be used in addition to the N-oxyl compound. Incidentally, N-hydroxy-2,2,6,6-tetramethyl piperidine compounds and 2,2,6,6-tetramethyl piperidine compounds may be contained as impurities in commercially available products of N-oxyl compounds. In this case, the use of such a commercially available product of N-oxyl compound amounts to the additional use of an N-hydroxy-2,2,6,6-tetramethyl piperidine compound or a 2,2,6,6-tetramethyl piperidine compound.

When the Michael type adduct is decomposed into acrylic acid and/or an acrylic ester and/or an alcohol in the presence of an N-oxyl compound, this decomposition brings the advantage that the alcohol formed by this decomposition will not easily induce a reaction of intramolecular dehydration or a reaction of intermolecular dehydration to form such a by-product as an alkene or an ether.

The quantity of the N-oxyl compound to be used is preferably in the range of 0.01–20 mass %, more preferably 0.1–10 mass %, and particularly preferably 0.5–6 mass %, based on the total mass of a Michael type adduct represented by the formula [I] and [II] from the viewpoint of the efficiency and cost of the conversion. In this case, the method for adding the N-oxyl compound is not particularly restricted. The N-oxyl compound can be added to the decomposing tank in the form of solution which dissolves the N-oxyl, in the form of solid, or in the form of gas. The N-oxyl compound may be directly supplied to the decomposing tank or added to either of the steps which precede and follow the step of decomposition. As a way of adding the N-oxyl compound in the form of solution, the N-oxyl compound dissolved in a proper solvent can be used. Then, as a way of adding the N-oxyl compound in the form of gas, the method which comprises gasifying or subliming the N-oxyl compound, supplying the resultant gas into the pipe communicating with the decomposing tank, and allowing it to mix with the contents of the tank is available. As concrete examples of the solvent which can dissolve the N-oxyl compound mentioned above, acrylic acid, acrylic esters, alcohols, water, benzene, toluene, xylene, cyclohexane, acetone, methylethyl ketone, methylisobutyl ketone, n-hexane, and heptane may be cited. These solvents may be used either singly or in the form of a mixture.

The temperature at which the Michael type adduct is reacted in the presence of the copper salt and the alkali metal salt and/or the alkaline earth metal salt optionally in combination with the N-oxyl compound varies with the kind of the Michael type adduct subjected to the reaction and the pressure of reaction. Generally, this temperature is in the range of 100–250° C., preferably 120–200° C., and particularly preferably 130–180° C. If this temperature exceeds 250° C., preferably in the range of 0.01–20 mass %, more preferably 0.1–10 mass %, and particularly preferably 0.5–6 mass %, based on the total mass of a Michael type adduct represented by the formula [I] and [II] from the viewpoint of the efficiency and cost of the conversion. In this case, the method for adding the N-oxyl compound is not particularly restricted. The N-oxyl compound can be added to the decomposing tank in the form of solution which desolves the N-oxyl, in the form of solid, or in the form of gas. The N-oxyl compound may be directly supplied to the decomposing tank or added to either of the steps which precede and follow the steps of decomposition. As a way of adding the N-oxyl compound in the form of solution, the N-oxyl compound dissolved in a proper solvent can be used. Then, as a way of adding the N-oxyl compound in the form of gas, the method which comprises gasifying or subliming the N-oxyl compound, supplying the resultant gas into the pipe communicating with the decomposing tank, and allowing it to mix with the contents of the tank is available. As concrete examples of the solvent which can dissolve the N-oxyl compound mentioned above, acrylic acid, acrylic esters, alcohols, water, benzene, toluene, xylene, cyclohexane, acetone, methylethyl ketone, methylisobutyl ketone, n-hexane, and heptane may be cited. These solvents may be used either singly or in the form of a mixture.

The temperature at which the Michael type adduct is reacted in the presence of the copper salt and the alkali metal salt and/or the alkaline earth metal salt optionally in combination with the N-oxyl compound varies with the kind of the Michael type adduct subjected to the reaction and the pressure of reaction. Generally, this temperature is in the range of 100–250° C. preferably 120–200° C., and particularly preferably 130–180° C. If this temperature exceeds 250° C., there is a possibility of inducing the increase of a secondary reaction, decreasing the yield, and increasing impurities such as low boiling substances. As a result, the quality of the product will decline. Furthermore, there is a possibility that the formation of a highly viscous residue due to the heat congestion at a high temperature is induced, and the solidifying of the content in the reaction vessel which is an industrially unfavorable situation is also induced. Particularly, while it has been heretofore necessary to decompose the compound at a temperature of 180° C. or more, the decomposition of the present invention efficiently occurs at a lower temperature. Therefore, the method of the present invention excels in thermal efficiency. Conversely, if this temperature is less than 100° C., there is a possibility that the efficiency is degraded due to lower reaction rate, and the conversion into target compounds of acrylic acid do not proceed with satisfactory efficiency. The pressure during the course of the reaction is not particularly restricted. It is preferably in the range of 0.01–1000 kPa, preferably 0.1–500 kPa, and particularly preferably 1–200 kPa.

In this invention, a polymerization inhibitor is preferably used for the purpose of preventing the acrylic acid, which is formed in the reaction for decomposing the Michael type adduct in the presence of the copper salt, and the alkali metal salt and/or the alkaline earth metal salt, from being polymerized. The polymerization inhibitor to be used herein may be any of the polymerization inhibitors which are widely used popularly in the process for producing acrylic acid compounds. As concrete examples of the polymerization inhibitor, hydroquinone, methoxy hydroquinone, phenothiazine, and hydroxyamine may be cited. When the reaction of decomposition is carried out in the presence of molecular oxygen, the effect of polymerization inhibition can be enhanced. The quantity of the polymerization inhibitor to be used herein is not particularly restricted. Preferably, the total quantity of the polymerization inhibitor to be used is in the range of 0.01–15 mass % based on the quantity of the vapor of acrylic acid and esters thereof.

The present method for the decomposition may be adopted in batch process, semicontinuous process, or continuous process. The continuous process means a manner in which the recovery of the Michael type adduct is carried out continuously and the decomposition of the Michael type adduct is carried out likewise in the presence of the salt mentioned above. In this continuous process, the rate of the supply of the Michael type adduct and the rate of the decomposition thereof are preferred to be balanced. For the purpose of securing this balance, the method called reactive distillation is available. In the continuous process, the retention time in the decomposing tank is generally in the range of 0.1–60 hours, preferably 1–40 hours, and particularly preferably 5–30 hours. If this retention time exceeds 60 hours, there is a possibility that the ratio of the formation of a by-product is heightened, and the nature and behavior of the product is impaired. It is disadvantage in terms of the cost of the equipment when the decomposing tank is large. Conversely, if the retention time is less than 0.1 hour, it can induce a unsufficient decomposition yield.

The Michael type adduct mentioned above is a component, which is by-produced in the process for producing acrylic acid. The products of the decomposition of the Michael type adduct are raw material compounds for acrylic acid and target products themselves. By using the present method of decomposition in the process for producing acrylic acid, therefore, an acrylic acid excellent in the quality can be produced in high production efficiency. Thus, the second aspect of this invention concerns a method for the production of acrylic acid, which comprises a step of recovering a Michael type adduct of an acrylic acid formed in the process for producing acrylic acid or an ester and a step of decomposing the recovered Michael type adduct by the method of decomposition according to the first aspect of this invention. Optionally, this method further comprises a step of returning the acrylic acid obtained by decomposing the Michael type adduct to the acrylic acid subsequently to the step of decomposing the Michael type adduct. By incorporating in the method the step of recovering the Michael type adduct outside the system, the by-product, which caused a problem in the process for producing acrylic acid, can be removed. And, an increase of the temperature during the production and the deterioration of the product can be avoided. Furthermore, by returning the product of decomposition to the system for the process of producing acrylic acid, the efficiency of raw material can be enhanced.

Now, as one example of the method for the production of acrylic acid which comprises a step of recovering such a Michael type adduct and a step of decomposing the recovered adduct, a method of subjecting propylene and/or acrolein to gas phase catalytic oxidation thereby obtaining an acrylic acid-containing gas and subsequently refining this gas will be described below with reference to FIG. 1. Since the Michael type adduct has a higher boiling point than acrylic acid, it is recovered in the fraction containing high boiling substances during the process for producing acrylic acid.

First, propylene (190) and a molecular oxygen-containing gas are supplied to a catalytic gas phase reaction vessel (110) provided with an intermediate tube sheet to partition the reaction vessel into an upper and a lower chamber and subjected to catalytic gas phase oxidation thereby obtaining an acrylic acid-containing gas. The reaction gas is introduced into an acrylic acid collecting column (120) and brought into contact with water therein, with the result that the acrylic acid will be collected in an aqueous solution. Since this acrylic acid-containing solution contains acrolein as an impurity, it is introduced into an acrolein dissipating column (130) and caused to release acrolein by dissipation and afford an aqueous acrylic acid solution containing 30 mass % of water and 3.0 mass % of acetic acid. Then, the column bottom liquid of the acrolein dissipating column (130) is introduced into an azeotropic dehydrating column (140) and an azeotropic solvent is supplied thereto and they are subjected together to dehydration by distillation. Part of the water acrylic acid are expelled by distillation through the top of the azeotropic dehydrating column (140). Consequently, a column bottom liquid containing 97.5 mass % of acrylic acid, 0.03 mass % of acetic acid, 0.02 mass % of water, and 2.45 mass % of other components is obtained. Subsequently, this column bottom liquid is introduced into a refining column (150) and acrylic acid (200) produced therein is obtained through the top thereof. The column bottom liquid of the refining column (150) is a liquid containing the Michael type adduct such as a dimer of acrylic acid. In this liquid, a dimer of acrylic acid, a trimer of acrylic acid, acrylic acid, maleic acid, and such other substances as a stabilizer and a high boiling substance are contained.

In this invention, the column bottom liquid containing the Michael type adduct is introduced into the middle of a high-boiling separating column (160) furnished with a membrane vaporizer (170). The column bottom liquid of the membrane vaporizer (170) which contains the Michael type adduct is introduced into a thermal decomposing column (180) while the bottom temperature of the high-boiling separating column (160) is continuously controlled by the working temperature of the membrane vaporizer (170). A copper dialkyldithiocarbamate and sodium acrylate, for example, are added respectively as a copper salt and an alkali metal salt and/or an alkaline earth metal salt to the interior of the thermal decomposing column (180). The temperature inside the thermal decomposing column is preferably in the range of 120–150° C. The decomposing column (180) may be provided with a heat source (not shown) for the purpose of retaining or elevating the temperature of the interior thereof. Since the liquid formed by the thermal decomposition contains acrylic acid and other components, part of this liquid is circulated to the membrane vaporizer (170) and the acrylic acid expelled by distillation through the top of the high-boiling separating column (160) is circulated to the azeotropic dehydrating column (140). Part of the liquid in the decomposing column is extracted as a waste liquid (300) from the system.

Figure 2:
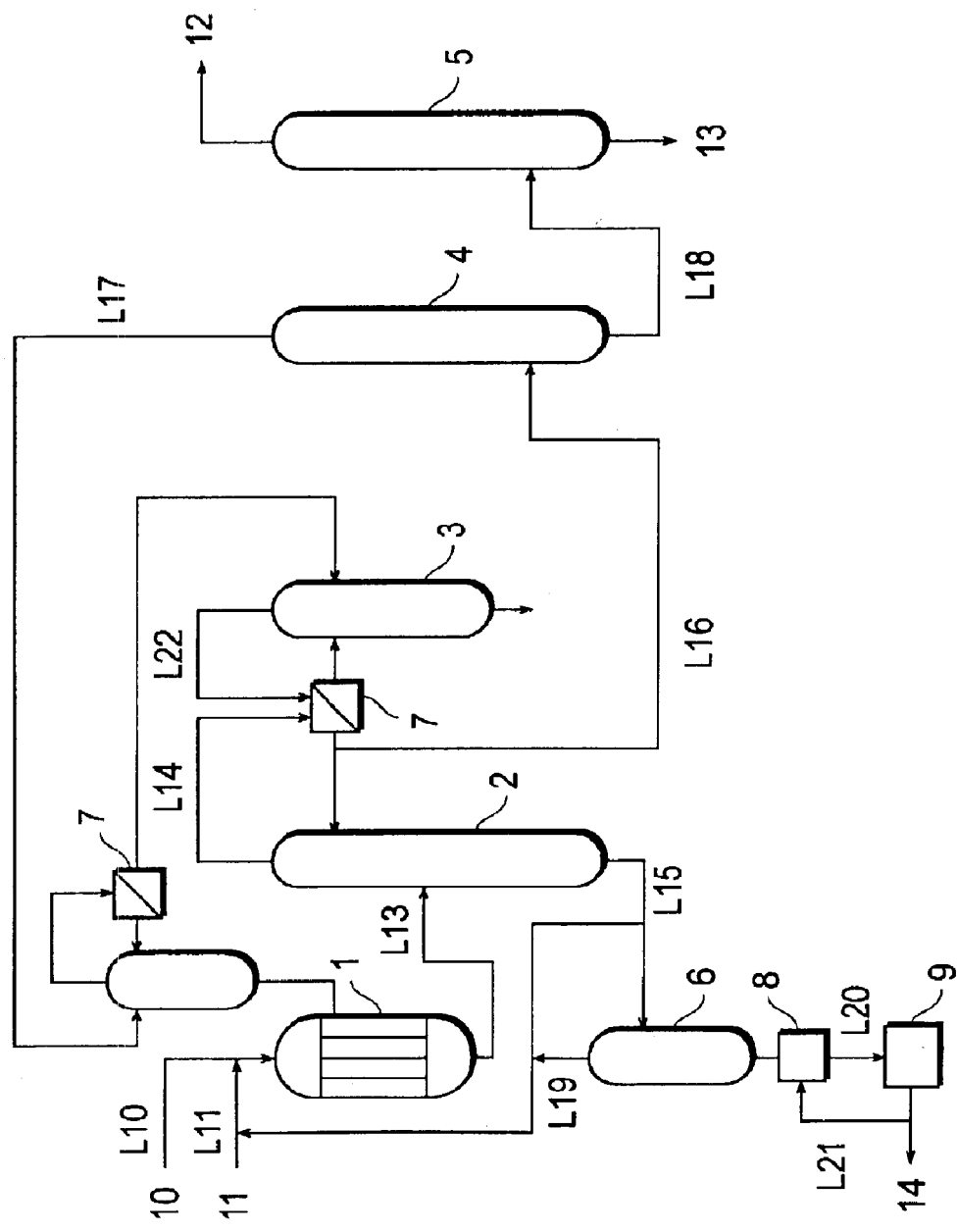
FIG. 2 is a schematic diagram showing the process for producing an acrylic ester.

As one example of the method for producing an acrylic ester which comprises forming acrylic acid by the reaction of catalytic gas phase oxidation and subsequently esterifying the acrylic acid will be described below with reference to FIG. 2.

Acrylic acid (11) is supplied via a line (L11) and an alcohol is supplied via a line (L10) both to an ester forming vessel (1) which is packed with a strongly acidic cation-exchange resin as a catalyst so as to induce formation of a product of esterification through the catalyst. The interior of the ester forming vessel (1) contains acrylic acid and an alcohol as raw materials for the production of the ester, an acrylic ester as the reaction product, and the by-produced water. Then, the reaction solution is introduced via a line (L13) into an acid separating column (2) and the column bottom liquid of this column containing a high-boiling substance is introduced into a high-boiling separating column (6) so as to expel by distillation an acrylic ester, an unaltered alcohol, and light boiling substances such as water through the top of the separating column. When the distillate is introduced via a line (L14) into an oil-water separating vessel (7), it is separated into an oil phase containing the acrylic ester and a water phase containing the water and the alcohol as main components. The water phase is transferred to an alcohol recovering column (3) and, the oil phase is supplied via a line (L16) to a low-boiling separating column (4). At this time, part of the oil phase may be refluxed to the acid separating column (2). Meanwhile, the acrylic ester is extracted through the bottom of the light-boiling separating column (4) and supplied via a line (L18) to a refining column (5) so as to induce distillation of an acrylic ester (12) as the product through the top of the refining column. The alcohol which is expelled by distillation through the top of the alcohol recovering column (3) is circulated via a line (L22) to the oil phase of the oil-water separating vessel (7). The water, alcohol, and other light-boiling substance which have been expelled by distillation through the top of the low-boiling separating column (4) are circulated to the ester forming vessel (1) through the distilling column disposed above the ester forming vessel (1).

In the process for producing this acrylic ester, the column bottom liquid of the acid separating column (2) which has been introduced into the high-boiling separating column (6) contains the Michael type adducts such as a dimer of acrylic acid, an ester thereof, an alkoxypropionic acid and an alkoxypropionic ester together with raw material such as acrylic acid. So, the column bottom liquid containing the Michael type adducts is introduced into the high-boiling separating column (6) provided with a membrane vaporizer (8) and distilled therein so as to expel acrylic acid by distillation through the top of the column and recover it. At the same time, the column bottom liquid containing the Michael type adducts is introduced into the membrane vaporizer (8) and subjected to further distillation to obtain the column bottom liquid. The column bottom liquid is introduced via a line (L20) into a thermal decomposing column (9) and heated therein together with a copper dialkyl-dithiocarbamate as a copper salt and sodium acrylate as an alkali metal salt, with the result that the Michael type adducts are decomposed into raw material components such as acrylic acid and alcohol and acrylic esters. When the products of the thermal decomposition are introduced into the membrane vaporizer (6), the alcohol, acrylic acid, and acrylic esters are expelled by distillation through the top of the the high-boiling separating column (6). The distillate is circulated via a line (L19) and the line (L11) to the ester forming vessel (1). Particularly, the return of the mixture of the products of the thermal decomposition to the step for esterification or acid separation brings the advantage of enabling the components to be separated at the next step or later. These components may be separated by methods such as distillation and extraction and put to use.

The expression "step for recovering Michael type adduct" used herein refers to a step for obtaining a fraction containing the Michael type adduct and even embraces a step for introducing the fraction containing the Michael type adduct into a decomposing column, for example. Thereafter, the Michael type adduct contained in the fraction is decomposed into acrylic acid in the presence of a copper salt, and an alkali metal salt and/or an alkaline earth metal salt.

This invention concerns a method for decomposing the Michael type adduct, and the Michael type adduct is produced in the process for producing acrylic acid as described above. By adding the copper salt, and the alkali metal salt and/or the alkaline earth metal salt to the process of production, therefore, it is made possible to decompose the Michael type adduct and produce acrylic acid and an ester thereof in accordance with the method of decomposition contemplated by this invention.

Incidentally, as a method for producing an acrylic ester, the method for producing the ester by subjecting acrylic acid and an alcohol to a dehydration reaction may be cited. As concrete examples of the preferred alcohol, various alcohols such as methanol, ethanol, n-butanol, iso-butanol, sec-butanol, tert-butanol, 1-pentanol, 2-pentanol, 3-pentanol, cyclopentanol, 1-hexanol, 2-hexanol, 3-hexanol, cyclohexanol, 1-heptanol, 2-heptanol, 3-heptanol, 1-octanol, iso-octanol, 2-ethylhexanol, iso-nonyl alcohol, and lauryl alcohol may be cited. These alcohols may be in a straight configuration or a branched configuration. These alcohols may be used either singly or in the form of a mixture.

Incidentally, the Michael type adduct as the target for the decomposition in the present invention is not restricted to the Michael type adduct, which is by-produced in the process for producing acrylic acid. It is, therefore, permissible to just react the Michael type adduct in a batch process in the presence of a copper salt and an alkali metal salt and/or an alkaline earth metal salt and decompose it to acrylic acid. In any process, the condition such as temperature and pressure mentioned above can be adopted to decompose the Michael type adduct to acrylic acid

EXAMPLES

Now, this invention will be specifically described below with reference to examples.

Example 1

A Michael type adduct of acrylic acid was decomposed by a batch process. First, in a round flask having an inner volume of 500 ml and fitted with a cooling pipe, 1.5 g of sodium acrylate and 1.5 g of a copper dibutyldithiocarbamate salt (hereinafter abbreviated as "CB") each as a catalyst and 297 g of a Michael type adduct (composed of 60 mass % of dimer of acrylic acid d (hereinafter abbreviated as "DAA"), 4 mass % of acrylic acid, 2 mass % of hydroquinone, and 34 mass % of other high-boiling impurities) were placed and reacted by stirring at a temperature of 140° C.

After four hours from the start of the reaction, the decomposition liquid was analyzed by gas chromatography. The results of the analysis are shown in Table 1. The degree of conversion and the degree of selectivity given in Table 1 were calculated by the following formulas.

$$\text{Degree of conversion \%} = \frac{\text{Mass of Michael type adduct decomposed}}{\text{Mass of Michael type adduct before decomposition}} \times 100$$

$$\text{Degree of selectivity \%} = \frac{\text{Total mass of formed acrylic acid, acrylic ester, alcohol}}{\text{Mass of Michael type adduct before decomposition}} \times 100$$

Example 2

A Michael type adduct was decomposed by a batch process. The decomposition of the Michael type adduct was performed by following the procedure of Example 1 except for that 1.5 g of 4-hydroxy-2,2,6,6-tetramethyl piperidinoxyl (hereinafter abbreviated as "4H-TEMPO") was further added as a catalyst. The results are shown in Table 1. Incidentally, the Michael type adduct had the same composition as in Example 1.

Comparative Example 1

A Michael type adduct was decomposed by a batch process. The decomposition of the Michael type adduct was performed by following the procedure of Example 1 except for that the sodium acrylate was not used as a catalyst. The results are shown in Table 1. Incidentally, the Michael type adduct had the same composition as in Example 1.

Comparative Example 2

A Michael type adduct was decomposed by a batch process. The decomposition of the Michael type adduct was performed by following the procedure of Example 1 except for that the copper dibutyldithiocarbamate was not used as a catalyst. The results are shown in Table 1. Incidentally, the Michael type adduct had the same composition as in Example 1.

Comparative Example 3

A Michael type adduct was decomposed by a batch process. The decomposition of the Michael type adduct was performed by following the procedure of Example 1 except for that neither the sodium acrylate nor the copper dibutyldithiocarbamate was used as catalysts. The results are shown in Table 1. Incidentally, the Michael type adduct had the same composition as in Example 1.

Example 3

A Michael type adduct of acrylic acid was decomposed by destructive distillation. First, a decomposing column (1000 mL flask) having a 20-shelf distilling column disposed thereover and provided with a stirrer was charged with 500 g of a Michael type adduct (composed of 60 mass % of DAA, 4 mass % of acrylic acid, 2 mass % of hydroquinone, and 34 mass % of other high-boiling impurities). With the decomposing column so controlled as to assume a working pressure of 35 hPa and a decomposing temperature of 140° C., the Michael type adduct, sodium acrylate, and copper dibutyldithiocarbamate salt (in the form dissolved in the Michael type adduct) were continuously injected at respectively ratios of 245 g/h, 1.2 g/h, and 1.2 g/hr into the bottom of the distilling column. At the same time, the acrylic acid formed by the decomposition was expelled by distillation through the top of the distilling column. At the time that the reflux ratio reached 1, the distillate and the extract from the distilling column were sampled and analyzed by gas chromatography. The results are shown in Table 1.

Comparative Example 4

A Michael type adduct was decomposed by destructive distillation. The decomposition of the Michael type adduct was performed by following the procedure of Example 3 except for that neither the sodium acrylate nor the copper dibutyldithiocarbamate was used. The results are shown in Table 1. Incidentally, the Michael type adduct had the same composition as in Example 1.

TABLE 1

| | Reaction temperature [° C.] | Sodium acrylate | CB | 4H-TEMPO | Degree of conversion DAA [%] | Degree of selectivity [%] |
|---|---|---|---|---|---|---|
| Example 1 | 140 | Yes | Yes | No | 63 | 80 |
| Example 2 | 140 | Yes | Yes | Yes | 70 | 85 |
| Example 3 | 140 | Yes | Yes | No | 66 | 82 |
| Comparative Example 1 | 140 | No | Yes | No | 45 | 65 |
| Comparative Example 2 | 140 | Yes | No | No | 50 | 60 |
| Comparative Example 3 | 140 | No | No | No | 30 | 54 |
| Comparative Example 4 | 140 | No | No | No | 45 | 60 |

Example 4

Acrylic acid was produced by following the flow of production of acrylic acid illustrated in FIG. 1.

A column bottom liquid containing a Michael type adduct was introduced at a rate of 0.8 ton/h into the middle of a high-boiling separating column (160) incorporating 15 vertically superposed sieve plates of stainless steel and provided with a membrane vaporizer (170). The high-boiling separating column (160), after assuming a bottom temperature of 90° C. through control of the membrane vaporizer (170), was operated under such conditions as an operating pressure of 35 hPa and a reflux ratio of 1. Further, the column bottom liquid of the membrane vaporizer (170) containing a Michael type adduct were introduced into a thermal decomposing column (180). Part of the liquid in this decomposing column was introduced again into the membrane vaporizer (170) via a line (L190). To this line (L190), an aqueous sodium acrylate solution (37 mass %) and copper dibutyl-dithiocarbamate (2 mass %, with acrylic acid used as a solvent) were added in quantities each accounting for 15 mass % based on the mass of a Michael type adduct-containing waste liquid (300) extracted through the bottom of the thermal decomposing column (180) and were eventually introduced into the thermal decomposing column. With the interior of the thermal decomposing column adjusted to a temperature of 150° C. and normal pressure, the Michael type adduct was decomposed into acrylic acid.

The acrylic acid thus formed by the thermal decomposing was recovered through the top of the high-boiling separating column (160) into the feed liquid to an azeotropic dehydrating column (140). Part of the liquid was extracted as waste liquid (300) from the system.

The entire disclosure of Japanese Patent Application No. 2002-124301 filed on Apr. 25, 2002 including specification, claims, drawings, and summary are incorporated herein by reference in its entirety.

What is claimed is:

1. A method for the decomposition of an adduct of an acrylic acid and/or an acrylic ester represented by the following formula [I] or [II], wherein decomposing the adduct in the presence of at least one copper salt and at least one metal salt selected from the group consisting of an alkali metal salt and an alkaline earth metal salt into an acrylic acid and/or an acrylic ester and/or an alcohol used as raw materials in production or a relevant acrylic and/or acrylic ester $$CH_2=CHCOO(-X-COO)_n-R^1 \qquad [I]$$

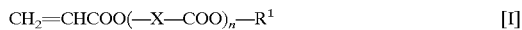

wherein n denotes an integer in the range of 1–5, $R^1$ denotes a hydrogen ato or an alkyl group, and —X— denotes —$CH_2CH_2$— or —$CH(CH_3)$—, and —X— may be identical or different when n is 2 or more.

$$R^2-O(-X-COO)_m-R^3 \qquad [II]$$

wherein m denotes an integer in the range of 1–5, $R^2$ and $R^3$ independently denote a hydrogen atom or an alkyl group, and —X— denotes —$CH_2CH_2$— or —$CH(CH_3)$—, and —X— may be identical or different when n is 2 or more.

2. A method according to claim 1, wherein decomposing the adduct in the presence of 4,4'.4'-tris-(2,2.6,6-tetramethyl piperidinoxyl) phosphite or 2,2,6,6-tetramethyl piperidinoxyls represented by the following formula (1)

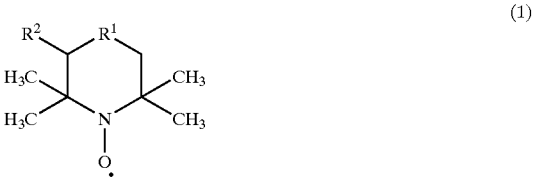

(1)

wherein $R^1$ denotes $CH_2$, CHOH, $CHCH_2OH$, $CHCH_2$, $CH_2OH$, $CHOCH_2OH$. $CHOCH_2CH_2OH$, CHCOOH, or C=O and $R^2$ denotes a hydrogen atom or $CH_2OH$ in addition to the copper salt and the metal salt selected from the group consisting of an alkali metal salt and an alkaline earth metal salt.

3. A method for the production of an acrylic acid and/or an acrylic ester, which comprises a step of recovering an adduct of an acrylic acid and/or an acrylic ester formed in the process for producing acrylic acid or an acrylic ester and a step of decomposing the recovered adduct of an acrylic acid and/or an acrylic ester in the presence of at least one copper salt and at least one metal salt selected from the group consisting of an alkali metal salt and alkaline earth metal salt into an acrylic acid and/or an acrylic ester and/or an alcohol used as raw materials in the production of a relevant acrylic acid and/or acrylic ester.

4. A method according to claim 3, which further comprises, subsequently to the step of decomposing the adduct of an acrylic acid and/or an acrylic ester, a step of returning at least one compound selected from the group consisting of the acrylic acid, the acrylic ester, and the alcohol obtained by the decomposition of the adduct of an acrylic acid and/or an acrylic ester to a step in the process for producing an acrylic acid and an acrylic ester.

* * * * *